United States Patent
Cucin

(10) Patent No.: US 9,925,314 B2
(45) Date of Patent: Mar. 27, 2018

(54) METHOD OF PERFORMING INTRA-ABDOMINAL TISSUE ASPIRATION TO AMELIORATE THE METABOLIC SYNDROME, OR ABDOMINAL OBESITY

(75) Inventor: Robert L. Cucin, West Palm Beach, FL (US)

(73) Assignee: Rocin Laboratories, Inc., West Palm Beach, FL (US)

(*) Notice: Subject to any disclaimer, the term of this patent is extended or adjusted under 35 U.S.C. 154(b) by 622 days.

(21) Appl. No.: 13/314,524

(22) Filed: Dec. 8, 2011

(65) Prior Publication Data

US 2012/0184943 A1 Jul. 19, 2012

Related U.S. Application Data

(63) Continuation of application No. 12/462,596, filed on Aug. 5, 2009, now Pat. No. 8,348,929.

(51) Int. Cl.
*A61B 5/01* (2006.01)
*A61M 1/00* (2006.01)
(Continued)

(52) U.S. Cl.
CPC ....... *A61M 1/0058* (2013.01); *A61B 18/1402* (2013.01); *A61B 18/148* (2013.01);
(Continued)

(58) Field of Classification Search
CPC ..... A61B 5/01; A61B 5/14539; A61B 5/1459; A61B 5/413; A61B 2017/0096;
(Continued)

(56) References Cited

U.S. PATENT DOCUMENTS

| 792,327 A | 6/1905 | Goodnow |
| 2,768,162 A | 10/1956 | Evans |

(Continued)

FOREIGN PATENT DOCUMENTS

| EP | 0125070 A2 | 11/1984 |
| FR | 2627087 A1 | 8/1989 |

(Continued)

OTHER PUBLICATIONS

Adipokines: the missing link between insulin resistance and obesity by Antuna-Puente B., Feve B., Fellahi S., Bastard J.P.; Inserm U680, faculte de medecine Saint-Antoine, university Pierre-et Marie Curie, Paris 6, 75012, Paris, France: Diabetes Metab. Feb. 2008; 34(1): 2-11. 10 page.

(Continued)

*Primary Examiner* — Tatyana Zalukaeva
*Assistant Examiner* — Ilya Treyger
(74) *Attorney, Agent, or Firm* — Thomas J. Perkowski, PC Esq, PC

(57) ABSTRACT

A method of safely removing mesenteric fat from the intra-abdominal region of human patients to ameliorate the metabolic syndrome, or abdominal obesity. The method involves using laparoscopically-guided intra-abdominal tissue aspiration, involving the simultaneously infusion of a tumescent solution into the mesenteric region of treatment, while synchronizing that infusion with the forward or return stroke of the inner cannula of the twin cannula assembly of a bipolar electro-cauterizing twin-cannula tissue aspiration instrument.

4 Claims, 8 Drawing Sheets

(51) Int. Cl.
*A61B 18/14* (2006.01)
*A61F 5/44* (2006.01)
*A61M 25/00* (2006.01)
*A61M 27/00* (2006.01)
*A61B 18/00* (2006.01)

(52) U.S. Cl.
CPC . *A61B 18/1477* (2013.01); *A61B 2018/00464* (2013.01); *A61B 2018/00595* (2013.01); *A61B 2018/1425* (2013.01); *A61B 2218/002* (2013.01); *A61B 2218/007* (2013.01)

(58) Field of Classification Search
CPC ......... A61F 5/44; A61M 1/00; A61M 1/0001; A61M 1/0005; A61M 1/0013; A61M 1/0023; A61M 1/008; A61M 1/0084; A61M 1/0088; A61M 25/002; A61M 25/0017; A61M 25/0111; A61M 27/00; A61M 2013/00536; A61M 2202/08; A61M 2205/8206
USPC .......................................... 604/313, 540–544
See application file for complete search history.

(56) References Cited

U.S. PATENT DOCUMENTS

| | | |
|---|---|---|
| 2,768,754 A | 10/1956 | Briggs |
| 2,895,162 A | 7/1959 | Harris |
| 2,895,182 A | 7/1959 | Harris |
| 3,082,805 A | 3/1963 | Royce |
| 3,401,684 A | 9/1968 | Dremann |
| 3,561,429 A | 2/1971 | Jewett et al. |
| 3,699,968 A | 10/1972 | Boldouc |
| 3,732,858 A | 5/1973 | Banko |
| 3,734,099 A | 5/1973 | Bender |
| 3,815,604 A | 6/1974 | O et al. |
| 3,833,000 A | 9/1974 | Bridgman |
| 3,889,657 A | 6/1975 | Baumgarten |
| 3,890,712 A | 6/1975 | Lopez |
| 3,937,222 A | 2/1976 | Banko |
| 3,937,322 A | 2/1976 | Cohen |
| 3,938,505 A | 2/1976 | Jamshidi |
| 3,945,375 A | 3/1976 | Banko |
| 3,955,579 A | 5/1976 | Bridgman |
| 3,994,297 A | 11/1976 | Kopf |
| 4,007,742 A | 2/1977 | Banko |
| 4,007,743 A | 2/1977 | Blake |
| 4,019,514 A | 4/1977 | Banko |
| 4,030,162 A | 6/1977 | Hubbard |
| 4,033,706 A | 4/1978 | Wiley |
| 4,083,706 A | 4/1978 | Wiley |
| 4,117,843 A | 10/1978 | Banko |
| 4,167,943 A | 9/1979 | Banko |
| 4,167,944 A | 9/1979 | Banko |
| 4,177,814 A | 12/1979 | Knepshield et al. |
| 4,203,444 A | 5/1980 | Bonnell |
| 4,210,146 A | 7/1980 | Banko |
| 4,274,414 A | 6/1981 | Johnson |
| 4,311,140 A | 1/1982 | Bridgman |
| 4,314,560 A | 2/1982 | Helfgott |
| 4,316,465 A | 2/1982 | Dotson, Jr. |
| 4,368,734 A | 1/1983 | Banko |
| 4,463,759 A | 8/1984 | Garito |
| 4,513,745 A | 4/1985 | Amoils |
| 4,517,977 A | 5/1985 | Frost |
| 4,530,356 A | 7/1985 | Helfgott et al. |
| 4,536,180 A | 8/1985 | Johnson |
| 4,549,554 A | 10/1985 | Markham |
| 4,562,838 A | 1/1986 | Walker |
| 4,568,332 A | 2/1986 | Shippert |
| 4,577,629 A | 3/1986 | Martinez |
| 4,617,013 A | 10/1986 | Betz |
| 4,644,951 A | 2/1987 | Bays |
| 4,651,753 A | 3/1987 | Lifton |
| 4,657,016 A | 4/1987 | Garito |
| 4,664,951 A | 5/1987 | Doehler |
| 4,674,502 A | 6/1987 | Imonti |
| 4,696,298 A | 9/1987 | Higgins et al. |
| 4,708,147 A | 11/1987 | Haaga |
| 4,710,162 A | 12/1987 | Johnson |
| 4,714,595 A | 12/1987 | Anthony |
| 4,735,605 A | 4/1988 | Swartz |
| 4,744,789 A | 5/1988 | Johnson |
| 4,754,754 A | 7/1988 | Garito |
| 4,764,165 A | 8/1988 | Reimels |
| 4,775,365 A | 10/1988 | Swartz |
| 4,792,327 A | 12/1988 | Swartz |
| 4,815,462 A | 3/1989 | Clark |
| 4,817,631 A | 4/1989 | Schnepp-Pesch et al. |
| 4,834,703 A | 5/1989 | Dubrul et al. |
| 4,350,373 A | 7/1989 | Zatioukal |
| 4,850,354 A | 7/1989 | McGurk-Burleson |
| 4,850,373 A | 7/1989 | Zatloukal et al. |
| 4,851,753 A | 7/1989 | Hamilton |
| 4,886,491 A | 12/1989 | Parisi |
| 4,886,492 A | 12/1989 | Brooke |
| 4,888,492 A | 12/1989 | Brooke |
| 4,893,535 A | 1/1990 | De Groot |
| 4,893,635 A | 1/1990 | De Groot et al. |
| 4,909,249 A | 3/1990 | Akkas et al. |
| 4,919,129 A | 4/1990 | Weber |
| 4,919,146 A | 4/1990 | Rhinehart et al. |
| 4,926,877 A | 5/1990 | Bookwalter |
| 4,932,935 A | 6/1990 | Swartz |
| RE33,258 E | 7/1990 | Onik |
| 4,938,743 A | 7/1990 | Lee |
| 4,940,468 A | 7/1990 | Petillo |
| 4,985,027 A | 1/1991 | Dressel |
| 4,986,827 A | 1/1991 | Akkas et al. |
| 4,989,614 A | 2/1991 | Dejter, Jr. et al. |
| 5,013,300 A | 5/1991 | Williams |
| 5,024,652 A | 6/1991 | Dumenek |
| 5,027,827 A | 7/1991 | Cody et al. |
| 5,052,999 A | 10/1991 | Klein |
| 5,095,901 A | 3/1992 | Davitashvili |
| 5,102,410 A | 4/1992 | Dressel |
| 5,106,364 A | 4/1992 | Hayafuji et al. |
| 5,112,302 A | 5/1992 | Cucin |
| 5,134,996 A | 8/1992 | Bell |
| 5,154,664 A | 10/1992 | Hazenbroek et al. |
| 5,171,660 A | 12/1992 | Carpenter |
| 5,176,677 A | 1/1993 | Wuchinich |
| 5,183,052 A | 2/1993 | Terwilliger |
| 5,186,714 A | 2/1993 | Boudreault |
| 5,213,110 A | 5/1993 | Kedem et al. |
| 5,226,429 A | 7/1993 | Kuzmak |
| 5,236,414 A | 8/1993 | Takasu |
| 5,243,994 A | 9/1993 | Ranalletta |
| 5,254,117 A | 10/1993 | Rigby et al. |
| 5,275,607 A | 1/1994 | Lo et al. |
| 5,275,609 A | 1/1994 | Pingleton et al. |
| 5,284,156 A | 2/1994 | Schramm et al. |
| 5,285,795 A | 2/1994 | Ryan et al. |
| 5,290,282 A | 3/1994 | Casscells |
| 5,295,955 A | 3/1994 | Rosen |
| 5,295,980 A | 3/1994 | Ersek |
| 5,300,069 A | 4/1994 | Hunsberger et al. |
| 5,304,207 A | 4/1994 | Stromer |
| 5,329,943 A | 7/1994 | Johnson |
| 5,348,022 A | 9/1994 | Leigh et al. |
| 5,348,535 A | 9/1994 | Cucin |
| 5,352,194 A | 10/1994 | Greco et al. |
| 5,356,638 A | 10/1994 | Gershenson |
| 5,358,638 A | 10/1994 | Gershenson |
| 5,386,388 A | 10/1994 | Gershenson |
| 5,364,395 A | 11/1994 | West |
| 5,372,945 A | 12/1994 | Alchas et al. |
| 5,380,277 A | 1/1995 | Phillips |
| 5,401,273 A | 3/1995 | Shippert |
| 5,403,276 A | 4/1995 | Schechter et al. |
| 5,411,513 A | 5/1995 | Ireland et al. |
| 5,429,596 A | 7/1995 | Arias et al. |
| 5,433,844 A | 7/1995 | Christy |

(56) References Cited

U.S. PATENT DOCUMENTS

| | | |
|---|---|---|
| 5,456,267 A | 10/1995 | Stark |
| 5,458,112 A | 10/1995 | Weaver |
| 5,464,300 A | 11/1995 | Crainich |
| 5,472,416 A | 12/1995 | Blugerman |
| 5,490,453 A | 2/1996 | Mackay |
| 5,505,210 A | 4/1996 | Clement |
| 5,514,084 A | 5/1996 | Fisher |
| 5,514,086 A | 5/1996 | Parisi |
| 5,520,685 A | 5/1996 | Wojciechowicz |
| 5,562,503 A | 10/1996 | Ellman |
| 5,643,198 A | 7/1997 | Cucin |
| 5,643,304 A | 7/1997 | Schechter et al. |
| 5,649,547 A | 7/1997 | Ritchart et al. |
| 5,655,544 A | 8/1997 | Johnson |
| 6,655,544 B1 | 8/1997 | Johnson |
| 5,665,100 A | 9/1997 | Yoon |
| 5,669,876 A | 9/1997 | Schechter et al. |
| 5,669,923 A | 9/1997 | Gordon |
| 5,689,923 A | 9/1997 | Gordon |
| 5,685,838 A | 11/1997 | Peters et al. |
| 5,685,840 A | 11/1997 | Schechter et al. |
| 5,697,383 A | 12/1997 | Manders |
| 5,720,762 A | 2/1998 | Bass |
| 5,730,717 A | 3/1998 | Gelbfish |
| 5,743,886 A | 4/1998 | Lynn |
| 5,746,762 A | 5/1998 | Bass |
| 5,769,086 A | 6/1998 | Ritchart et al. |
| 5,769,879 A | 6/1998 | Richards et al. |
| 5,775,333 A | 7/1998 | Burbank et al. |
| 5,776,092 A | 7/1998 | Farin |
| 5,779,649 A | 7/1998 | Herbert |
| 5,782,849 A | 7/1998 | Miller |
| 5,788,651 A | 8/1998 | Weilandt |
| 5,792,603 A | 8/1998 | Dunkelman |
| 5,795,323 A | 8/1998 | Cucin |
| 5,797,907 A | 8/1998 | Clement |
| 5,807,275 A | 9/1998 | Jamshidi |
| 5,807,353 A | 9/1998 | Schmitz |
| 5,810,806 A | 9/1998 | Ritchart et al. |
| 5,810,809 A | 9/1998 | Rydell |
| 5,843,111 A | 12/1998 | Vijfvinkel |
| 5,848,978 A | 12/1998 | Cecchi |
| 5,865,803 A | 2/1999 | Major |
| 5,893,862 A | 4/1999 | Pratt et al. |
| 5,911,699 A | 6/1999 | Anis et al. |
| 5,911,700 A | 6/1999 | Mozsary et al. |
| 5,911,701 A | 6/1999 | Miller et al. |
| 5,913,857 A | 6/1999 | Ritchart et al. |
| 5,916,229 A | 6/1999 | Evans |
| 5,928,164 A | 7/1999 | Burbank et al. |
| 5,928,218 A | 7/1999 | Gelbfish |
| 5,944,673 A | 8/1999 | Gregoire et al. |
| 5,944,748 A | 8/1999 | Mager |
| 5,954,686 A | 9/1999 | Garito |
| 5,964,716 A | 10/1999 | Gregoire et al. |
| 5,971,939 A | 10/1999 | Desantis et al. |
| 5,980,469 A | 11/1999 | Burbank et al. |
| 5,980,545 A | 11/1999 | Pacala et al. |
| 5,980,546 A | 11/1999 | Hood |
| 5,997,560 A | 12/1999 | Miller |
| 6,017,316 A | 1/2000 | Ritchart et al. |
| 6,019,733 A | 2/2000 | Farascioni |
| 6,022,324 A | 2/2000 | Skinner |
| 6,033,375 A | 3/2000 | Brumbach |
| 6,050,955 A | 4/2000 | Bryan et al. |
| 6,063,108 A | 5/2000 | Salansky |
| 6,076,544 A | 6/2000 | Pierce |
| 6,077,230 A | 6/2000 | Gregoire et al. |
| 6,080,113 A | 6/2000 | Heneveld et al. |
| 6,085,749 A | 7/2000 | Wardle et al. |
| 6,086,544 A | 7/2000 | Hibner et al. |
| 6,096,042 A | 8/2000 | Herbert |
| 6,102,885 A | 8/2000 | Bass |
| 6,109,446 A | 8/2000 | Foote |
| 6,113,569 A | 9/2000 | Becker |
| 6,120,462 A | 9/2000 | Hibner et al. |
| 6,120,463 A | 9/2000 | Bauer |
| 6,121,042 A | 9/2000 | Peterson |
| 6,139,518 A | 10/2000 | Mozsary et al. |
| 6,142,955 A | 11/2000 | Farascioni et al. |
| 6,149,610 A | 11/2000 | Urko |
| 6,152,142 A | 11/2000 | Tseng |
| 6,162,187 A | 12/2000 | Buzzard et al. |
| 6,182,187 B1 | 12/2000 | Buzzard |
| 6,190,364 B1 | 2/2001 | Imbert |
| 6,203,518 B1 | 3/2001 | Anis et al. |
| 6,204,375 B1 | 3/2001 | Lader |
| 6,208,903 B1 | 3/2001 | Richards et al. |
| 6,210,409 B1 | 4/2001 | Ellman |
| 6,213,971 B1 | 4/2001 | Poole |
| 6,231,571 B1 | 5/2001 | Ellman |
| 6,238,388 B1 | 5/2001 | Ellman |
| 6,238,394 B1 | 5/2001 | Garito |
| 6,261,302 B1 | 7/2001 | Voegele et al. |
| 6,270,471 B1 | 8/2001 | Hechel et al. |
| 6,273,862 B1 | 8/2001 | Privitera et al. |
| 6,273,882 B1 | 8/2001 | Privitera |
| 6,290,690 B1 | 9/2001 | Huculak |
| 6,293,944 B1 | 9/2001 | Ellman |
| 6,293,957 B1 | 9/2001 | Peters et al. |
| 6,302,863 B1 | 10/2001 | Tankovich |
| 6,315,756 B1 | 11/2001 | Tankovich |
| 6,316,247 B1 | 11/2001 | Katz et al. |
| 6,331,165 B1 | 12/2001 | Turturro et al. |
| 6,346,078 B1 | 2/2002 | Ellman |
| 6,346,107 B1 | 2/2002 | Cucin |
| 8,022,324 B2 | 2/2002 | Skinner |
| 6,352,533 B1 | 3/2002 | Ellman |
| 6,371,911 B1 | 4/2002 | Hossain et al. |
| 6,379,372 B1 | 4/2002 | Dehdashtian et al. |
| 634,973 A1 | 5/2002 | Cucin |
| 6,387,093 B1 | 5/2002 | Ellman |
| 6,394,973 B1 | 5/2002 | Cucin |
| 6,395,002 B1 | 5/2002 | Ellman |
| 6,402,701 B1 | 6/2002 | Kaplan et al. |
| 6,425,883 B1 | 7/2002 | Urich |
| 6,428,487 B1 | 8/2002 | Burdorff et al. |
| 6,432,105 B1 | 8/2002 | Ellman |
| 6,447,510 B1 | 9/2002 | Ellman |
| 6,450,941 B1 | 9/2002 | Larsen |
| 6,461,350 B1 | 10/2002 | Underwood et al. |
| 6,468,225 B1 | 10/2002 | Lundgren |
| 6,468,227 B2 | 10/2002 | Zimmon |
| 6,471,069 B2 | 10/2002 | Lin et al. |
| 6,471,700 B1 | 10/2002 | Burbank et al. |
| 6,471,716 B1 | 10/2002 | Pecukonis |
| 6,478,681 B1 | 11/2002 | Overaker et al. |
| 6,482,200 B2 | 11/2002 | Shippert |
| 6,485,436 B1 | 11/2002 | Truckai et al. |
| 6,494,876 B1 | 12/2002 | Fowler et al. |
| 6,503,240 B1 | 1/2003 | Niedospial, Jr. et al. |
| 8,503,240 B2 | 1/2003 | Niedospial |
| 6,514,215 B1 | 2/2003 | Ouchi |
| 6,520,935 B1 | 2/2003 | Jansen et al. |
| 6,620,935 B1 | 2/2003 | Jansen |
| 6,544,211 B1 | 4/2003 | Andrew et al. |
| 6,544,246 B1 | 4/2003 | Niedospial, Jr. |
| 6,554,803 B1 | 4/2003 | Ashman |
| 6,592,508 B1 | 7/2003 | Ravins et al. |
| 6,605,080 B1 | 8/2003 | Altshuler et al. |
| 6,626,890 B2 | 9/2003 | Nguyen et al. |
| 6,632,182 B1 | 10/2003 | Treat |
| 6,638,235 B2 | 10/2003 | Miller et al. |
| 6,638,238 B1 | 10/2003 | Weber et al. |
| 6,838,238 B1 | 10/2003 | Weber |
| 6,652,522 B2 | 11/2003 | Cucin |
| 6,663,659 B2 | 12/2003 | McDaniel |
| 6,676,629 B2 | 1/2004 | Andrew et al. |
| 6,697,670 B2 | 2/2004 | Chomenky et al. |
| 6,714,803 B1 | 3/2004 | Mortz |
| 6,743,245 B2 | 6/2004 | Lobdell |
| 6,752,768 B2 | 6/2004 | Burdorff et al. |
| 6,758,824 B1 | 7/2004 | Miller et al. |
| 6,761,701 B2 | 7/2004 | Cucin |

(56) References Cited

U.S. PATENT DOCUMENTS

| | | |
|---|---|---|
| 6,786,405 B2 | 9/2004 | Wiedenhoefer |
| 6,795,728 B2 | 9/2004 | Chornenky et al. |
| 6,817,996 B2 | 11/2004 | Fard |
| 6,835,202 B2 | 12/2004 | Harth |
| 6,872,199 B2 | 3/2005 | Cucin |
| 6,875,207 B2 | 4/2005 | Weber et al. |
| 6,892,099 B2 | 5/2005 | Jaafar et al. |
| 6,899,723 B2 | 5/2005 | Chen |
| 6,902,559 B2 | 6/2005 | Taufig |
| 6,916,328 B2 | 7/2005 | Brett |
| 6,951,611 B2 | 10/2005 | Dannenmaier et al. |
| 6,992,233 B2 | 1/2006 | Drake |
| 7,018,395 B2 | 3/2006 | Chen |
| 7,037,344 B2 | 5/2006 | Kagan et al. |
| 7,041,217 B1 | 5/2006 | Close et al. |
| 7,048,683 B2 | 5/2006 | Borst et al. |
| 7,060,061 B2 | 6/2006 | Altshuler et al. |
| 7,060,079 B2 | 6/2006 | Wulc et al. |
| 7,081,128 B2 | 7/2006 | Hart |
| 7,112,200 B2 | 9/2006 | Cucin |
| 7,166,576 B2 | 1/2007 | Cicardi et al. |
| 7,175,081 B2 | 2/2007 | Andreasson et al. |
| 7,181,271 B2 | 2/2007 | Berg et al. |
| 7,226,424 B2 | 6/2007 | Ritchart et al. |
| 7,241,616 B2 | 7/2007 | Ohno et al. |
| 7,258,674 B2 | 8/2007 | Cribbs et al. |
| 7,295,872 B2 | 11/2007 | Kelly et al. |
| 7,306,740 B2 | 12/2007 | Freund |
| 7,311,722 B2 | 12/2007 | Larsen |
| 7,381,206 B2 | 6/2008 | Cucin |
| 7,384,417 B2 | 6/2008 | Cucin |
| 7,390,484 B2 | 6/2008 | Fraser et al. |
| 7,473,420 B2 | 1/2009 | Fraser et al. |
| 7,488,427 B2 | 2/2009 | Freund |
| 7,501,115 B2 | 3/2009 | Fraser et al. |
| 7,514,075 B2 | 4/2009 | Hedrick et al. |
| 7,595,043 B2 | 9/2009 | Hedrick et al. |
| 7,639,136 B1 | 12/2009 | Wass et al. |
| 7,651,664 B2 | 1/2010 | Hedrick |
| 7,651,684 B2 | 1/2010 | Hedrick et al. |
| 7,678,070 B2 | 3/2010 | Kumar et al. |
| 7,687,059 B2 | 3/2010 | Fraser et al. |
| 7,712,674 B1 | 5/2010 | Warner et al. |
| 7,718,617 B2 | 5/2010 | Cicardi et al. |
| 7,740,605 B2 | 6/2010 | Cucin |
| 7,767,208 B2 | 8/2010 | Chen |
| 7,771,716 B2 | 8/2010 | Hedrick et al. |
| 7,775,973 B2 | 8/2010 | Okada et al. |
| 7,779,845 B2 | 8/2010 | Ortiz |
| 7,780,649 B2 | 8/2010 | Shippert |
| 7,780,684 B2 | 8/2010 | Wule et al. |
| 7,789,872 B2 | 9/2010 | Shippert |
| 7,794,449 B2 | 9/2010 | Shippert |
| 7,824,848 B2 | 11/2010 | Owen et al. |
| 7,883,476 B2 | 2/2011 | Miller et al. |
| 7,887,795 B2 | 2/2011 | Fraser et al. |
| 7,896,890 B2 | 3/2011 | Ortiz et al. |
| 7,901,672 B2 | 3/2011 | Fraser et al. |
| 7,951,590 B2 | 5/2011 | Gen |
| 7,988,633 B2 | 8/2011 | Hossack et al. |
| 7,990,272 B2 | 8/2011 | Wass et al. |
| 8,062,286 B2 | 11/2011 | Shippert |
| 8,099,297 B2 | 1/2012 | Brevnova et al. |
| 8,105,580 B2 | 1/2012 | Fraser et al. |
| 8,113,424 B2 | 2/2012 | Philippe |
| 8,119,121 B2 | 2/2012 | Fraser et al. |
| 8,133,339 B2 | 3/2012 | Dorian |
| 8,133,389 B2 | 3/2012 | Dorian et al. |
| 8,152,821 B2 | 4/2012 | Gambale et al. |
| 8,182,450 B2 | 5/2012 | Moosheimer et al. |
| 8,268,612 B2 | 9/2012 | Owen et al. |
| 8,288,612 B2 | 9/2012 | Owen |
| 8,348,929 B2 | 1/2013 | Cucin |
| 8,465,471 B2 | 6/2013 | Cucin |
| 8,574,223 B2 | 11/2013 | Cucin |
| 7,445,831 B2 | 9/2016 | Mark |
| 2001/0014785 A1 | 8/2001 | Sussman et al. |
| 2001/0031976 A1 | 10/2001 | Lobdell |
| 2002/0045840 A1 | 4/2002 | Voegele et al. |
| 2002/0077565 A1 | 6/2002 | Burdorff et al. |
| 2002/0082519 A1 | 6/2002 | Miller et al. |
| 2002/0103486 A1 | 8/2002 | Cucin |
| 2002/0120212 A1 | 8/2002 | Ritchart et al. |
| 2002/0128632 A1 | 9/2002 | Cucin |
| 2002/0138047 A1 | 9/2002 | Lopez |
| 2002/0151874 A1 | 10/2002 | Kolster et al. |
| 2002/0156365 A1 | 10/2002 | Tsekos |
| 2002/0156385 A1 | 10/2002 | Tsekos |
| 2002/0173814 A1 | 11/2002 | Jung et al. |
| 2003/0018281 A1 | 1/2003 | Huitema |
| 2003/0069543 A1 | 4/2003 | Carpenter et al. |
| 2003/0073929 A1 | 4/2003 | Baltschun et al. |
| 2003/0078609 A1 | 4/2003 | Finlay et al. |
| 2003/0087423 A1 | 5/2003 | Haywood et al. |
| 2003/0088235 A1 | 5/2003 | Tazi |
| 2003/0105454 A1 | 6/2003 | Cucin |
| 2003/0125639 A1 | 7/2003 | Fisher et al. |
| 2003/0144606 A1 | 7/2003 | Kadziauskas et al. |
| 2003/0187383 A1 | 10/2003 | Weber et al. |
| 2004/0049128 A1 | 3/2004 | Miller et al. |
| 2004/0073195 A1 | 4/2004 | Cucin |
| 2004/0167516 A1 | 8/2004 | Cucin |
| 2004/0222137 A1 | 11/2004 | Hashimoto |
| 2004/0267562 A1 | 12/2004 | Fuhrer et al. |
| 2005/0004632 A1 | 1/2005 | Benedict |
| 2005/0049521 A1 | 3/2005 | Miller et al. |
| 2005/0054995 A1 | 3/2005 | Barzell et al. |
| 2005/0075703 A1 | 4/2005 | Larsen |
| 2005/0113715 A1 | 5/2005 | Schwindt et al. |
| 2005/0165345 A1 | 7/2005 | Laufer |
| 2005/0175665 A1 | 8/2005 | Hunter |
| 2005/0175703 A1 | 8/2005 | Hunter |
| 2005/0178395 A1 | 8/2005 | Hunter |
| 2005/0178396 A1 | 8/2005 | Hunter |
| 2005/0182463 A1 | 8/2005 | Hunter |
| 2005/0183731 A1 | 8/2005 | Hunter |
| 2005/0186244 A1 | 8/2005 | Hunter |
| 2005/0187140 A1 | 8/2005 | Hunter |
| 2005/0196421 A1 | 9/2005 | Hunter |
| 2005/0197648 A1 | 9/2005 | Cucin |
| 2005/0208095 A1 | 9/2005 | Hunter |
| 2005/0233298 A1 | 10/2005 | Farsedakis |
| 2005/0256445 A1 | 11/2005 | Cucin |
| 2005/0266494 A1 | 12/2005 | Hodge |
| 2005/0267446 A1 | 12/2005 | Cucin |
| 2006/0093527 A1 | 5/2006 | Buss |
| 2006/0155210 A1 | 7/2006 | Beckman et al. |
| 2006/0247514 A1 | 11/2006 | Panasyuk et al. |
| 2007/0005082 A1 | 1/2007 | Kraemer et al. |
| 2007/0055292 A1 | 3/2007 | Ortiz et al. |
| 2007/0123850 A1 | 5/2007 | Cucin |
| 2007/0129735 A1 | 6/2007 | Filipi et al. |
| 2007/0167963 A1 | 7/2007 | Deem et al. |
| 2007/0175486 A1 | 8/2007 | Cox |
| 2007/0175488 A1 | 8/2007 | Cox et al. |
| 2007/0225686 A1 | 9/2007 | Shippert |
| 2007/0239176 A1 | 10/2007 | Stokes et al. |
| 2008/0027353 A1 | 1/2008 | Kliman |
| 2008/0033758 A1 | 2/2008 | Keeley |
| 2008/0154240 A1 | 6/2008 | Shippert |
| 2008/0154292 A1 | 6/2008 | Huculak et al. |
| 2009/0076486 A1 | 3/2009 | Cucin |
| 2009/0093790 A1 | 4/2009 | Massengale |
| 2009/0124975 A1 | 5/2009 | Oliver |
| 2009/0157002 A1 | 6/2009 | Dumot |
| 2009/0192498 A1 | 7/2009 | Andrew et al. |
| 2009/0192854 A1 | 7/2009 | Pietrucha, Jr. et al. |
| 2009/0228030 A1 | 9/2009 | Shadeck |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0121420 A1 | 5/2010 | Fiset |
| 2010/0210745 A1 | 8/2010 | McDaniel |
| 2010/0331883 A1 | 12/2010 | Schmitz |

(56) References Cited

U.S. PATENT DOCUMENTS

| | | |
|---|---|---|
| 2010/0331928 A1 | 12/2010 | Dunning |
| 2011/0034905 A1 | 2/2011 | Cucin |
| 2011/0118542 A1 | 5/2011 | Cucin |
| 2011/0159562 A1 | 6/2011 | Deisseroth |
| 2011/0213336 A1 | 9/2011 | Cucin |
| 2011/0306950 A1 | 12/2011 | Cucin |
| 2012/0101479 A1 | 4/2012 | Paspaliaris et al. |
| 2012/0150103 A1 | 6/2012 | Cucin |
| 2012/0150152 A1 | 6/2012 | Cucin |
| 2012/0157944 A1 | 6/2012 | Cucin |
| 2013/0006225 A1 | 1/2013 | Cucin |
| 2013/0041265 A1 | 2/2013 | Sostek |

FOREIGN PATENT DOCUMENTS

| | | |
|---|---|---|
| FR | 2648050 A | 12/1990 |
| WO | 2009092092 A1 | 7/2009 |
| WO | 2011017517 A1 | 2/2011 |

OTHER PUBLICATIONS

Adipose expression of tumor necrosis factor-alpha: direct role in obesity-linked insulin resistance (Abstract). Hotamisligil GS, Shargill N.S, Spiegelman BM; Dana-Farber Cancer Institute, Boston MA; Science, Jan. 1, 1993, 259(509) 87-91, 1 page.

Adipose Tissue as an Endocrine Organ. By Erin E. Kershaw and Jeffrey S. Flier; Division of Endocrinology, Dept. of Medicine Beth Israel Deaconess Medical Center, Boston MA 02215; Journal of Clinical Endocrinology & Metabolism 89(6): pp. 2548-2556, Copyright 2004 by the Endocrine Society. 9 pages.

Amelioration of diet-induced diabetes mellitus by removal of visceral fat by Cid Pitombo, Eliana P. Araujo, Claudio T. De Souza, Jose C. Pareja, Bruno Geloneze and Lisle A. Vellose. Journal of Endocrinology (2006) 191, 699-706, Society for Endocrinology, printed in Great Britain, 8 pages.

Diabetes: insulin resistance and derangements in lipid metabolism. Cure through intervention in fat transport and storage. Raz I., Elder R., Cernea S., Shafrir E.; Dept. of Medicine, Diabetes Ctr., Hadassah University Hospital, Jerusalem 91120, Israel. ntv502@netvision.net.il. Diabetes Metab Res Rev. Jan.-Feb. 2005: 21(1) 3-14, 12 pages.

Effect of a multidisciplinary program of weight reduction on endothelial functions in obese women (Abstract). Nocoletti G., Pontillo A., Cioffi M., D'Andea F., Giugliano D., Esposito K., Chair of Plastic and Reconstructive Surgery, Second University of Naples, Naples Italy. J. Endocrinol Invest Mar. 2003; 26(3): RC5-88. 1 page.

Effect of Liposuction on insulin resistance and vascular inflammatory markers in obese women by G. Giugliano, G. Nicolletti, E Grelia, F. Giugliano, K. Esposito, N. Scuderi, F. D'Andrea; British Journal of Plastic Surgery, of. vol. 57, Issue 3, pp. 190-194, Apr. 2004. 5 pagess.

Effect of potentially modifiable risk factors associated with myocardial infarction in 52 countries (the INERHEART study): case-control study. Salim Yusuf, Steven Hawken, Stephanie Ounpuu, Tony Dans, Alvaro Avezum, Fernando Lanes, Matthew McQueen, Andrzej Budaj, Pram Pais, John Varigos, Liu Lisheng on behalf of the INTERHEART Study Investigators. Lancet 2004; vol. 364: 937-52. Published Online Sep. 3, 2004, Http://image:thelancet.com/extras/04art8001web.Pdf. 16 pages.

Guidelines on Laparoscopy, European Association of Urology, J.D. Doublet, G. Janetshek, A. Joyce, A. Mandressi, J. Rassweiller, D. Tolley, 2002, 38 pages.

Historical perspective: visceral obesity and related comorbidity in Joannes Bapista Morgagni's 'De sedibus et causis morborum per anatomen indagata' by Enzi G. Busetto L., Inelmen EM, Coin A., Sergi G.; Dept. of Medical and Surgical Sciences, Univ. of Padova, Italy. Int J Obes Relat Metab Disord. Apr. 2003; 27(4):534-5. 2 pages.

Human mesenteric adipose tissue plays unique role versus subcutaneous and omental fat in obesity related diabetes (Abstract). Yang YK, Chen M, Clements RH, Abrams GA, Aprahamian CJ, Harmon CM; Dept. of Surgery, Univ. of Alabama at Birmingham, USA. Cell Phys of Biochem, 2008; 22(5-6): 531-8. Epub Dec. 9, 2008. 1 page.

Improvements in cardiovascular risk profile after large-volume lipoplasty: a 1-year follow-up study by Giese SY, Neborsky R, Bulan EJ, Spear SL, Yanovsk, JA; Aesthet Surg J Nov. 2001 21(6): 527-31, 5 pages.

International Search Report in International Application No. PCT/US 11/62346 dated Jul. 2, 2012.

International Search Report, International Application No. PCT/US 10/44543, dated Jan. 6, 2011.

Large-Volume Liposuction and Extensive Abdominoplasty: a feasible alternative for improving body shape by Carenas-Camarena, Lazaro M.D.; Gonzalez, Luis M.D.; Plastic & Reconstructive Surgery: Oct. 1998—vol. 102—Issue 5—pp. 168-1707. 9 pages.

Leptin and the Regulation of Body Weight by Jeffrey M. Friedman, Rockefeller University, New York NY 10065 USA fried@mail.rockefeller.edu; Copyright 2011 by the Keo Journal of Medicine. 9 pages.

Mechanism of the Postreceptor Defect in Insulin Action in Human Obesity: Decrease in Glucose Transport System Activity; Theodore P. Ciaraldi, Orville G. Kolterman, and Jerrold M. Olefsky, Dept. of Medicine, University of Colorado Health Sciences Ctr., Div. of Endocrinology/Metabolism, Denver CO 80262; J. Clin. Invest. The American Soc. or Clinical Investigation, Inc., 0021-9738/81/10/0875/06, vol. 68, Oct. 1981, pp. 875-880. 6 pages.

Mediastinal Fat, Insulin Resistance, and Hypertension by Arya M. Sharma; Hypertension 2004, 44:117-118: originally published online Jul. 12, 2004 doi: 10.1161/01.HYP.0000137993.7045.82: Copyright 2004 American Heart Assn., ISN: 0194-911X. Online SSSN: 1524-4563. http://hyper.ahajournals.org/content/44/2/117. 3 pages.

Modification of insulin, glucose and cholesterol levels in nanobese women undergoing liposuction, is lipsuction metabolically safe? Robles-Cervantes JA, Yanez-Diaz S., Cardenas-Camarena L.; Ann Plast Surg. Jan. 2004; 52(1): 64-7. 4 pages.

Novel Interaction of Adiponectin with the Endocrine System and Inflammatory Parameters by Jose Manuel Fernandez-Real, Abel Lopez-Bermejo, Roser Casamitjana and Wifredo Ricart; Unit of Diabetes, Endocrinology and Nutrition, Dept. of Internal Medicine, University Hospital of Girona "Dr. Josep Trueta," 17007 Girona, Spain; The Journal of Clinical Endocrinology & Metabolism 88(6): 2714-2718; Copyright 2003 by The Endocrine Society doi: 10.1210/ic.2002-021583. 5 pages.

Obesity and the Risk of Cardiovascular Disease. Mitchell N. Rashid, MD; Francisco Fuetes, MD; Robert C. Tonchon; MD, Paulette S. Wehner MD; Dept. of Internal Medicine, Marshall University School of Medicine, Huntington WV; University of Texas, and the Dept. of Cardiovascular Medicine, Marshall University, Huntington WV. Preventive Cardiology Winter 2003. 6 pages.

Obesity in the new millennium (Abstract). Friedman JM. The Rockefeller University, New York NY 10021-6399 USA; Nature Apr. 6, 2000 404 (6778) 632-4. 1 page.

Omentectomy and Metabolic Syndrome. ClinicalTrialsFeeds.org, U.S. National Institute of Health Clinical Trials Search Delivered via RSS. Last Updated: Nov. 24, 2009, Verified by Instituto Nacional de Ciencias Medicas y Nutricion Salvador Zubiran, No. 2009. 10 pages.

Surgical removal of visceral adipose tissue: effects on insulin action. Gabriely I, Barzaila N.; Institute for Aging Research, Belfer Bldg. #701, Albert Einstein College of Medicine, 1300 Morris Park Avenue, Bronx NY 10461 USA. 6 pages.

The Breast-Q: Further Validation in Independent Clinical Samples. Stefan J. Cano, Ph.D., Anne F. Klassen, D. Phil., Amie M. Scott, M.P.H., Peter G. Cordeiro, M.D., Andrea L. Pusic, M.D. H.S.S.; Peninsula College of Medicine and Dentistry, McMaster University and Memorial Sloan Kettering Caner Center; Copyright 2012 by the American Society of Plastic Surgeons. DOI: 10.1097/PRS.0b013e31823 aec6b. 10 pages.

(56) References Cited

OTHER PUBLICATIONS

The effects of surgically removing subcutaneous fat on the metabolic profile and insulin sensitivity in obese women after large-volume liposuction treatment (Abstract). Gonzalez-Ortiz M., Robles-Cervantes JA, Cardenas-Camarena L., Bustos-Saldana R., Martinez-Abundis E.; Medial Research Unit in Clinical Epidemiology, West National Medical Center, Mexican Institute of Social Security, Guadalajara, Mexico. uiec@Prodigy.net.mx. Horn Metab Res. Aug. 2002; 34(8): 446-9. 1 page.

The role of TNF-alpha in insulin resistance. Borst SE. Dept. of Exercise & Sport Sciences, University of Florida, Malcom Randall VA Medical Center, Gainesville FL 32608-1197, USA seborst@ufi.edu; Endocrine Mar.-Apr. 2004; 23(2-3) 177-82. 6 pages.

Visceral adipose tissue modulates mammalian longevity. Radhikak Muzumdar, David B. Allison, Derek M. Huffman, Xiaohui MA, Gil Atzmon, Francine H. Einstein, Sigal Fishman, Aruna D. Poduval, Theresa McVei, Scott W. Keith, and Nir Barzilli, Inst. for Aging Research, Albert Einstein College of Medicine, Bronx NY, USA, Dept. of Medicine, Albert Einstein College of Medicine, Bronx NY, USA 3. Dept. of Pediatrics, Albert Einstein Collage of Medicine, Bronx NY, USA.

Modification of insulin, glucose and cholesterol levels in nonobese women undergoing liposuction, is liposuction metabolically safe? Robles-Cervantes JA, Yanez-Diaz S., Cardenas-Camarena L.; Ann Plast Surg. Jan. 2004; 52(1): 64-7. 4 pages.

Adipose expression of tumor necrosis factor-alpha: direct role in obesity-linked insulin resistance (Abstract). Hotamisligil GS, Shargill N. S, Spiegelman BM; Dana-Farber Cancer Institute, Boston MA; Science Jan. 1, 1993; 259 (509) 87-91. 1 page.

Obesity in the new millennium (Abstract). Friedman JM. The Rockefeller University, New York NY 10221-6399 USA; Nature Apr. 6, 2000 404 (6778) 632-4. 1 page.

Improvements in cardiovascular risk profile ater large-volume lipoplasty: a 1-year follow-up study by Giese SY, Neborsky R, Bulan EJ, Spear SL, Yankvski, JA; Aesthet Surg J Nov. 21, 2001(6): 527-31. 5 pages.

International Search Report dated Jul. 2, 2012 issued in International Application No. PCT/US 11/62345.

Notice of Allowance dated Jul. 7, 2017 for U.S. Appl. No. 13/315,224; (pp. 1-5).

Notice of Allowance dated Jul. 13, 2017 for U.S. Appl. No. 13/315,230; (pp. 1-5).

Notice of Allowance dated Jul. 6, 2017 for U.S. Appl. No. 13/315,232; (pp. 1-5).

Office Action dated Jul. 17, 2017 for U.S. Appl. No. 13/315,243; (pp. 1-6).

METHOD OF PERFORMING INTRA-ABDOMINAL TISSUE ASPIRATION TO AMELIORATE THE METABOLIC SYNDROME, OR ABDOMINAL OBESITY

RELATED CASES

This Application is a Continuation of application Ser. No. 12/462,596 filed Aug. 5, 2009, now U.S. Pat. No. 8,348,929 said Application is owned by Rocin Laboratories, Inc., and incorporated herein by reference in its entirety.

BACKGROUND OF THE INVENTION

Field of the Invention

The present invention relates to a novel way of and means for treating abdominal obesity and metabolic syndrome in human patients.

Brief Description of the State of Knowledge in the Art

In general, there are three kinds of fat in the human body: subcutaneous fat, intramuscular fat, and visceral fat.

Subcutaneous fat is found underneath the skin, and intramuscular fat is found interspersed in skeletal muscle. Fat in the lower body, e.g. in thighs and buttocks, is subcutaneous. Visceral fat, also known as organ fat or intra-abdominal fat, is located inside the peritoneal cavity, packed in between the internal organs and torso of the abdomen. There are several adipose tissue deposits of visceral fat in the human body, namely: mesenteric, epididymal white adipose tissue, and perirenal deposits. [Adipose tissue as an endocrine organ Kershaw E E, Flier J S. J. Clin. Endocrinol. Metab. 89 (6): 2548-56 (2004).] An excess of visceral fat is known as central obesity, "belly fat," the "pot belly" or "beer belly," where the abdomen protrudes excessively.

Over 250 years ago, Johannes Baptista Morgagni described android obesity as increased intra-abdominal and mediastinal fat accumulation. Back then, he recognized the association between visceral obesity, hypertension, hyperuricemia, atherosclerosis, and obstructive sleep apnea syndrome. [Historical perspective: visceral obesity and its relation to morbidity in Johannes Baptista Morgagni's 'De sedibus et causis morborum per anatomen indagata' Enzi G, Busetto L, Inelmen E M, Coin A, Sergi G Int. J. Obes Relat Metab Disord 27: 534-535 (2003)]

Today, Morgagni's android obesity condition is now described as metabolic syndrome, and is associated with insulin resistance and increased risk of Coronary Heart Disease. The Metabolic syndrome is a condition defined by any three of five risk factors, one of which is waist circumference (female waist>88 cm (>35"), male waist>102 cm. (>40"). The others are triglycerides: (men<40 mg/dl; women<50 mg/dl), HDL cholesterol (≥110 mg/dl), blood pressure (≥130/≥85 mm Hg), and FBS (>150 ml/dl). [Dyslipidemia of central obesity and insulin resistance. Brunzell, J D, Hokanson, J E Diabetes Care: 22(3); Mediastinal fat, insulin resistance and hypertension. Sharma A M Hypertension: 44:117 (2004)].

Over the past 40 years, the prevalence of obesity in the US increased from 13% to 32%. In 2003-2004, 66% of U.S. adults were overweight or obese.

Abdominal obesity as measured by waist circumference and waist hip ratio (WHR) is an independent predictor of mortality. Marginally increased waist circumference is strongly associated with prevalent hypertension in normal-weight and overweight adults. Also, there is a strong correlation between central (i.e. abdominal) obesity and cardiovascular disease. [Effect of potentially modifiable risk factors associated with myocardial infarction in 52 countries. Yusuf S, Hawken S, Ounpu S, Dans T, Avezum A, Lanas F, McQueen M, Budaj A, Pais P, Varigos J, Lisheng L, Lancet 364: 937-52 (2004).] Because of this, the WHR ratio has been used as a measure of obesity and is an indicator or measure of the health of a person, and the risk of developing serious health conditions. Research shows that people with "apple-shaped" bodies (with more weight around the waist) face more health risks than those with "pear-shaped" bodies who carry more weight around the hips. [Waist-hip ratio should replace Body Mass Index as an indicator of mortality risk in older people. Am. J. Clin. Nutrition (Aug. 12, 2006).]

A WHR of 0.7 for women and 0.9 for men have been shown to correlate strongly with general health and fertility. Women within the 0.7 range have optimal levels of estrogen and are less susceptible to major diseases such as diabetes, cardiovascular disorders and ovarian cancers. Men with WHR's around 0.9, similarly, have been shown to be more healthy and fertile with less prostate cancer and testicular cancer. Studies show that 80 percent of women over the age of 18 have a WHR of at least 0.9. This is a 40 percent increase since 2002, and it keeps increasing.

Although maintaining a healthy weight is a cornerstone in the prevention of chronic diseases and premature death, maintaining a healthy waist size should also be an important goal.

Markedly obese patients are typically directed towards diet and exercise programs, and failing that, presented with the option of bariatric surgery or living with and dying from the increased morbidity of obesity. After bariatric surgery, plastic surgeons perform skin excisions of the redundant folds of tissue remaining on patients who had lost 50-200 lbs. These post-bariatric surgery patients are frequently nutritional cripples with hypoalbuminemia, cirrhosis, and renal stones and suffer increased complications reflecting their impaired nutritional status.

Traditional plastic surgical approaches have been cosmetic, targeted only at removing (i) localized subcutaneous fat deposits in non-obese or modestly obese patients, and (ii) the redundant folds of abdominal wall or pannus that remain after massive weight loss from gastric banding or intestinal bypass procedures.

Before subcutaneous liposuction, combined hemostasis and analgesia is achieved in the patient by infusing tumescent solutions of lactated Ringer's solution, containing dilute amounts of xylocaine and epinephrine. Performing tumescent liposuction in this manner allows increased volumes of fat to be removed and obviates the need for general anaesthesia which, in turn, facilitates outpatient surgery in office-based facilities. [Tumescent Technique Klein, J. Mosby (2000).]

Studies have now shown large volume (subcutaneous) liposuction and abdominoplasty as feasible alternatives for improving body shape. [Large-volume liposuction and extensive abdominoplasty: a feasible alternative for improving body shape. Cardenas-Camarena L, Gonzalez L E Plast Reconstr Surg. 102: 1698-707 (1998).] Clinical studies have shown large volumes of fat can be safely removed in serial liposuction procedures performed at safe intervals. Pilot studies have also shown improvement in the cardiovascular risk profile with large volume subcutaneous liposuction. [Improvements in cardiovascular risk profile with large-volume liposuction: a pilot study. Giese S Y, Bulan E J, Commons G W, Spear S L, Yanovski J A. Plastic Reconstr Surg. 108 510-21 (2001).] However, it should be noted that such large volume subcutaneous liposuction approaches are still mainly cosmetic, as only the less metabolically active, subcutaneous fat is addressed and removed during such procedures.

Recently, animal research has discovered that only the removal of visceral fat in mice has been shown to stop insulin resistance. [Visceral fat removal stops insulin resistance. Barzilai N. Diabetes 51: 2951-2958 (2002).] Increased visceral fat shortens mammalian longevity and its removal lengthens it. [Visceral adipose tissue modulates mammalian longevity. Muzumdar R., Allison D B, Huffman, D M, Xiaohui M, Einstein, F H, Fishman S, Poduval A D, McVei T, Keith, S W, Barzilai, N. Aging Cell 7(3) 438-440 (2008).] [The effect of fat removal on glucose tolerance is depot specific in male and female mice. Haifei S, Strader A D, Woods, S C, Seeley, R J Am. J. Physiol Endocrinol Metab 293: E1012-1020 (2007).]

Also, in Brazil, clinical trials are being carried out with partial omentectomy to determine the effect on insulin sensitivity. However, such studies have used direct surgical excision, posing high risk of vascular injury, with concomitant bleeding and vascular compromise of the intestine. [Surgical removal of visceral fat tissue (omentectomy) associated to bariatric surgery: effect on insulin sensitivity. Clinical Trials NCT00545805 University of Campinas, Brazil.]

Thus, while there is great promise that the removal of visceral fat in the mesenteric region of human patients stands to ameliorate the metabolic syndrome and abdominal obesity, and reduce morbidity due to obesity, there is a great need in the art for a new and improved method of and apparatus for safely removing visceral fat in human patients, without employing direct surgical excision and posing high risk of vascular injury with concomitant bleeding and vascular compromise of the intestine, associated with conventional surgical procedures and apparatus.

OBJECTS OF THE PRESENT INVENTION

Accordingly, it is a primary object of the present invention to provide a new and improved method of and apparatus for safely removing mesenteric fat in human patients to ameliorate the metabolic syndrome, or abdominal obesity, while avoiding the shortcomings and drawbacks of conventional surgical procedures and apparatus.

Another object of the present invention is to provide such an apparatus in the form of a laparoscopically-guided intra-abdominal liposuction system including a powered hand-supportable instrument held by a surgeon and having an electro-cauterizing cannula assembly for the safe removal of visceral fat from the mesenteric region of a patient, through a small incision in the patient's body.

Another object of the present invention is to provide such a laparoscopically-guided intra-abdominal liposuction system, designed for safely removing visceral fat from the mesenteric region of a patient.

Another object of the present invention is to provide such a laparoscopically-guided intra-abdominal liposuction system, wherein the powered hand-supportable instrument has a bipolar electro-cauterizing cannula assembly, provided with a moving inner cannula, supported in a stationary outer cannula connected to the hand-supportable housing of the instrument.

Another object of the present invention is to provide a novel method of and apparatus for performing laparoscopic mesenteric liposuction for ameliorating the metabolic syndrome, or abdominal obesity of the patient.

Another object of the present invention is to provide such a method comprising the steps of inserting a laparoscopic instrument and an electro-cauterizing liposuction instrument into the mesenteric region of a patient, for the purpose of safely removing visceral fat to ameliorate the metabolic syndrome, or abdominal obesity of the patient.

Another object of the present invention is to provide a novel method of laparoscopically-guided intra-abdominal liposuction, involving the simultaneously infusion of a tumescent solution into the mesenteric region of treatment, while synchronizing that infusion with the forward or return ("action") stroke of the inner cannula of the twin (dual) cannula assembly of the instrument.

A further object of the present invention is to provide a novel system for removing both subcutaneous and visceral fat deposits in a minimally invasive manner.

Yet a further object of the present invention is to provide a novel method of minimally invasive liposuction which is equally applicable to both subcutaneous and visceral fat deposits.

These and other objects of the present invention will be described in greater detail hereinafter in the claims to invention appended hereto.

BRIEF DESCRIPTION OF THE DRAWINGS

The above Objects of the Present Invention will be more fully understood when taken in conjunction with the following FIGure Drawings, wherein like elements are indicated by like reference numbers, wherein:

FIG. 2B1 is a first cross-sectional view of the bipolar twin-cannula assembly shown in FIG. 2B;

FIG. 2B2 is a second cross-sectional view of the twin-cannula assembly shown in FIG. 2B;

FIG. 2B3 is an enlarged cross-sectional view of the distal portion of the twin-cannula assembly shown in FIG. 2B, showing its integrated irrigation channel, and irrigation aperture formed in the outer cannula of the twin-cannula assembly;

DETAILED DESCRIPTION OF THE ILLUSTRATIVE EMBODIMENTS OF THE PRESENT INVENTION

In general, the method of treatment according to the present invention involves performing vacuum-assisted aspiration of mesenteric fat from a patient, using either an "open direct-viewing" based laparotomy procedure, or minimally-invasive, "laparoscopic" based procedure.

The open direct-viewing based procedure involves a surgical team making a direct laparotomy incision into the abdomen of the patient using their own direct human vision to guide their surgical instruments, while performing a visceral liposuction procedure/method in accordance with the principles of the present invention.

The laparoscopic-based procedure involves a surgical team making one or more limited access portals into the patient's abdomen and using laparoscopic and/or camera monitor assistance for their human vision, while performing the visceral liposuction procedure/method in a minimally invasive fashion according to the principles of the present invention.

Using either method, visceral fat is safely removed from the mesenteric region of a patient to help to ameliorate the metabolic syndrome, and/or abdominal obesity.

Figure 1:
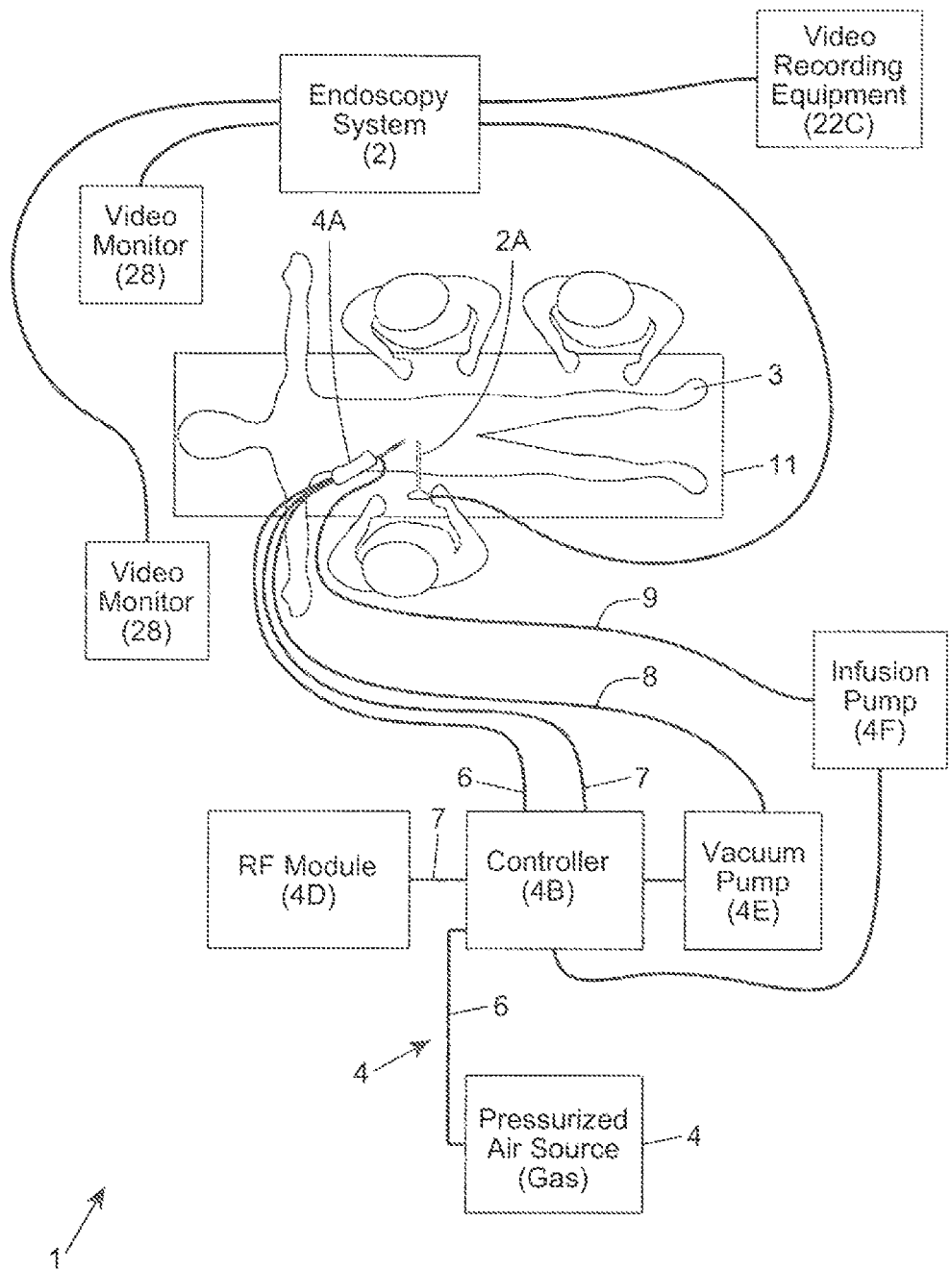
FIG. 1 is a system block diagram of the laparoscopically-guided bipolar power-assisted twin-cannula liposuction system of the present invention, showing an obese patient in an operating room undergoing a mesenteric liposuction procedure carried out using the same.
Figure 4:
FIG. 4 is a perspective view of the patient's abdominal region during the first phase of a mesenteric liposuction procedure of the present invention, showing the inspection of the small bowel and placing a region of proximal jejunum under tension between two graspers for treatment, following creation of routine laparoscopy portals and customary $CO_2$ infusion for abdominal distension.

In FIGS. 1 and 4, there is shown a preferred apparatus for performing either versions of the mesenteric liposuction method of the present invention, typically in an operating room environment.

As shown in FIGS. 1 and 2, the apparatus of the present invention 1 comprises: an endoscopy (e.g. laparoscopy) system, or laparoscope 2 having (i) video probe 2A for insertion into the patient 3, (ii) one or more video monitors (e.g. LCD displays and controller) 2B for displaying to surgeons and assistants, real-time digital color video images of the patient's abdominal region captured along the field of view (FOV) of the video probe 2A, and (iii) digital recording equipment 2C for recording captured digital video during the operation and marking the same by the surgeons, as required; a bipolar electro-cauterizing twin-cannula powered liposuction system 4 having (i) an air-powered hand-supportable instrument 4A provided with a self-irrigating bipolar electro-cauterizing twin-cannula assembly 5, (ii) a system controller 4B connected to the hand-supportable instrument 4A by way of a flexible multi-lumen cable assembly 4C, for supplying (i) pressurized air streams 6 to drive the inner cannula of the hand-supportable instrument 4A, and (ii) RF-power signals 7 generated by an RF signal generating module 4D for powering the self-irrigating bipolar electro-cauterizing twin cannula assembly 5, as taught in U.S. Pat. No. 7,384,417 B2; a vacuum line 4E connected to the base portion of the inner cannula via a flexible tubing, for aspirating visceral fat through the aspiration aperture 9 of the twin cannula assembly 5 during system operation; and an infusion pump 4F controlled by the system controller 4B, for periodically or continuously infusing solution near the distal portion of the cannula assembly 5 during system operation; an operating table 11 for supporting a patient; and other operating room equipment including high intensity lighting apparatus, refraction clips, stitches etc.

Figure 2A:
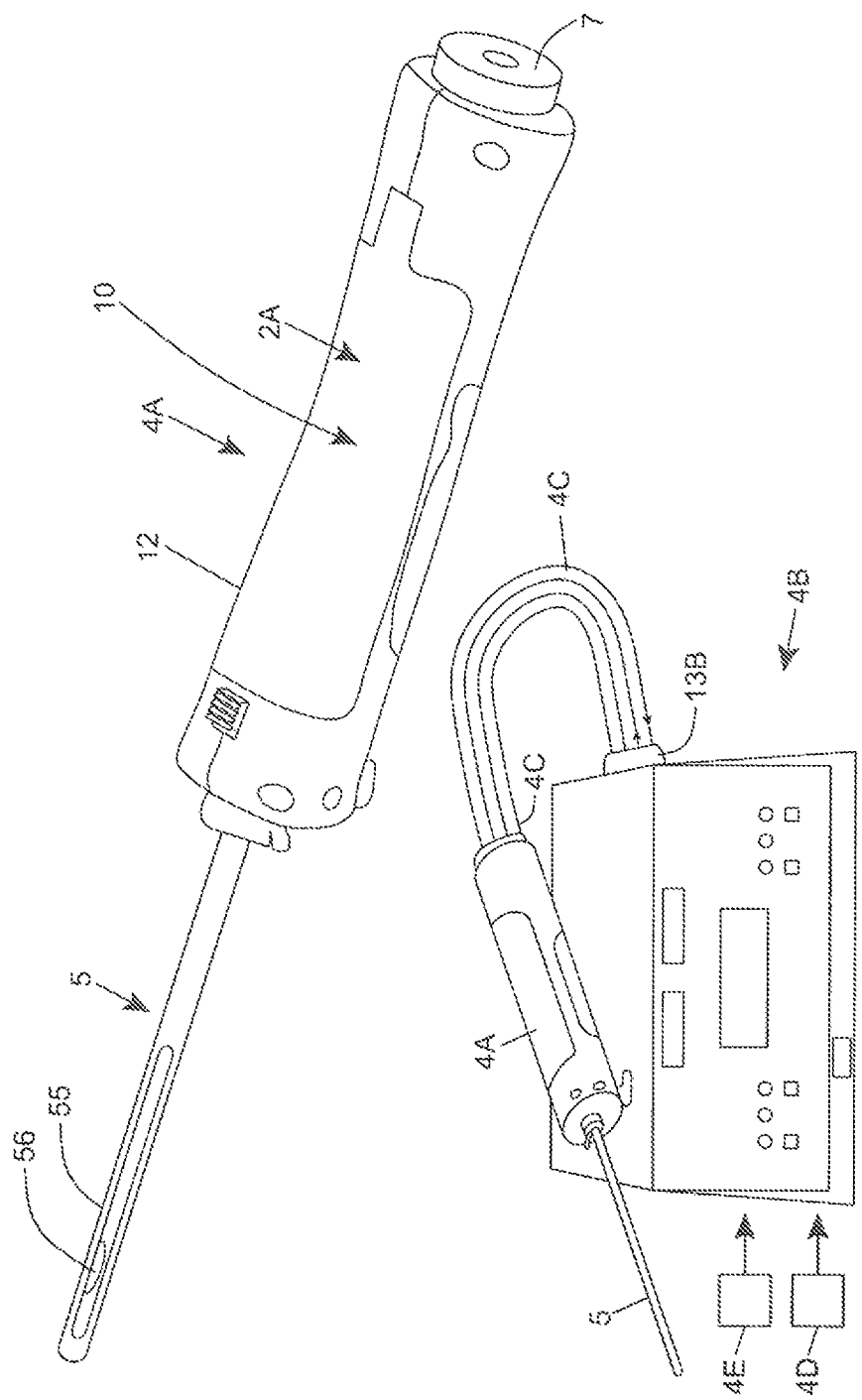
FIG. 2A is a perspective view of the bipolar electro-cauterizing irrigating twin-cannula liposuction instrumentation system of the present invention, shown in the system of FIG. 1, wherein an inner cannula is mechanically reciprocated within a stationary outer cannula of the hand-supportable instrument, while the inner cannula is operably affixed to a vacuum source and the hand piece is attached to a quick connect cable assembly that connects it to the (digital signal processor) DSP controller, providing a closed feedback loop for safe control of reciprocation rate and stroke, control of bipolar electro-cautery, and synchronized pulsed tumescent infusion during system operation.

In FIG. 2A, the hand-supportable electro-cautery liposuction instrument 4A of FIG. 1 is shown in greater detail. As shown, the instrument has a hand-supportable housing 12 into which the self-irrigating bipolar electro-cauterizing cannula assembly 5 is removably inserted by the surgeon. In the illustrative embodiment, the housing has a side panel which opens 12A for servicing. The rear portion of the housing has a connector 13A into which one end of the flexible cable assembly 4C snap-fits as taught in U.S. Pat. No. 7,384,417 B2. Within the housing, a motor 10 (i.e. inner cannula driving mechanism) is provided for reciprocating the inner cannula within the outer cannula during instrument operation. The "motor" 10, as defined herein and in the Claims to Invention, can be realized using any or more available motion-drive technologies such as, for example: a pressurized-air cylinder driven by source of pressurized gas (e.g. $CO_2$); an electromagnetic motor driven by electrical current delivered at a given voltage; or other powered-type device capable of reciprocating the inner cannula within the outer cannula assembly.

Figure 2B:
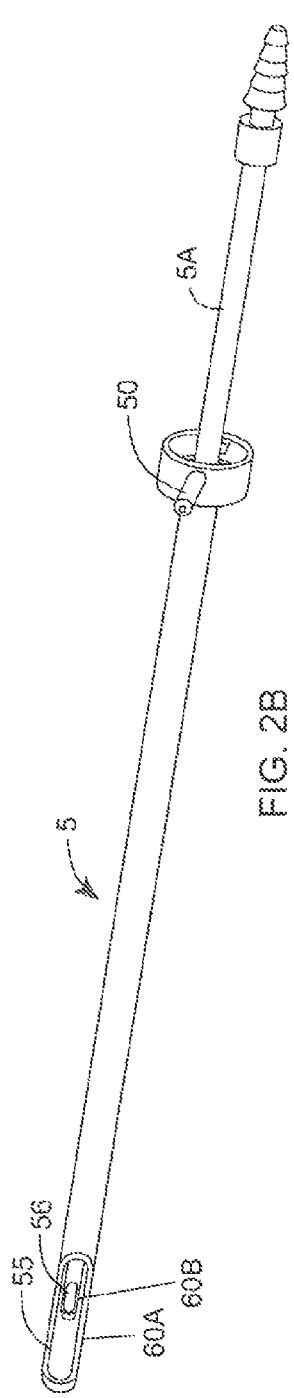
FIG. 2B is a perspective view of a bipolar electro-cauterizing twin-cannula assembly shown in FIG. 2, having bipolar electro-cauterizing electrodes formed about the aspiration aperture of the twin cannula assembly, and an integrated irrigation channel (lumen) formed in the outer wall portion of its outer cannula, and irrigation aperture formed at the distal tip portion thereof, for expressing irrigation fluid supplied to the irrigation channel from an irrigation fluid supply system.
Figure 2B:
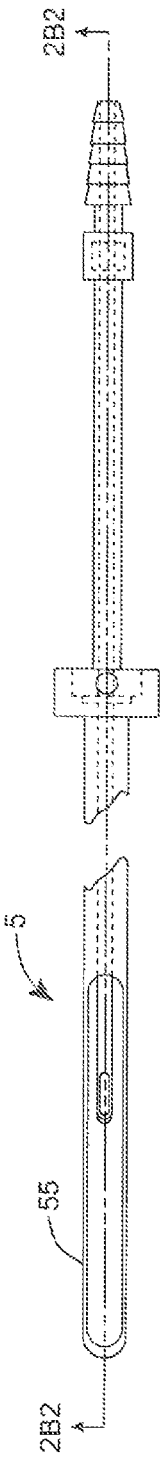
Figure 2B:
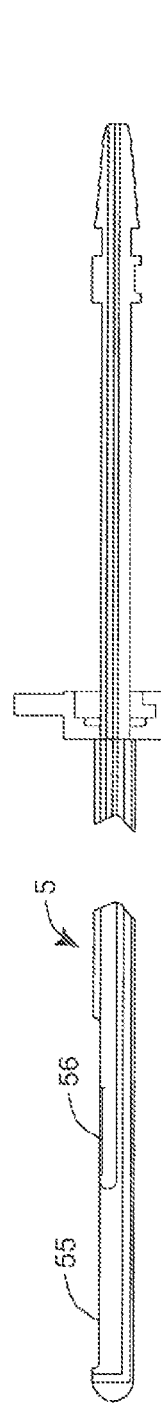
Figure 2B:
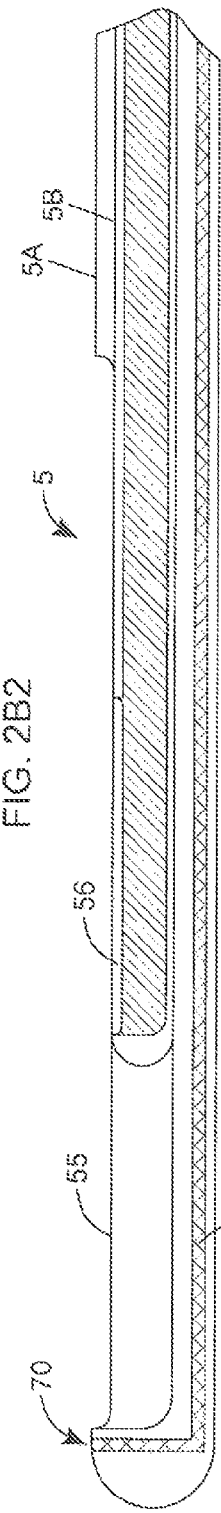

As shown in FIGS. 2B, 2B1 and 2B2, the bipolar electro-cauterizing cannula assembly 5 has a distal portion and an proximate portion, and includes an outer cannula 5A having a base portion that inserts within said hand-supportable housing and has an elongated aperture 56 formed at the distal portion of the outer cannula. The cannula assembly 5 also includes an inner cannula 5B supported within the outer cannula 5A, and having an aspiration aperture 55, and a base portion which is operably connected to vacuum pump 4E, by way of a flexible tubing 8, for aspirating visceral fat tissue from the mesentery of the patient. As shown in FIG. 2B, electrically-conductive electrodes 60A and 60B are formed along the elongated aperture 56 and aspiration aperture 55 of the outer and inner cannulas, respectively. The purpose of electrodes 60A and 60B is to electro-cauterize visceral fat tissue as the fat tissue is being aspiration through the aspiration aperture, with or without irrigation.

As shown in the illustrative embodiment of FIG. 2B3, a fluid or irrigation channel 69 is formed in the outer cannula 5A and terminates at the distal portion of the outer cannula lumen. However, in other embodiments of the present invention, the irrigation channel 69 can be formed externally to the outer cannula 5A, and terminate at the distal portion thereof, to deliver irrigation fluid in the region where the aspiration aperture 56 reciprocates during instrument operation. As shown in FIG. 2B, the base portion of the outer cannula 5A has a small irrigation connector 50 for receiving the open end portion of a length of flexible tubing 9 supplying the irrigation fluid to the outer cannula 5A, as part of the infusion pump system 4F.

During system operation, the infusion pump 4F delivers controlled amounts of fluid to the irrigation channel 69, over short periods of time, in synchronization with either the forward or return stroke of the inner cannula 5B within the outer cannula 5A, so that fluid flows out of the irrigation aperture 70 and proximate to the elongated aperture 56, while visceral fat is being electro-cauterized by electrodes 60A and 60B and aspirated through the reciprocating aspiration aperture 55 of the hand-supportable liposuction instrument 5.

Figure 2C:
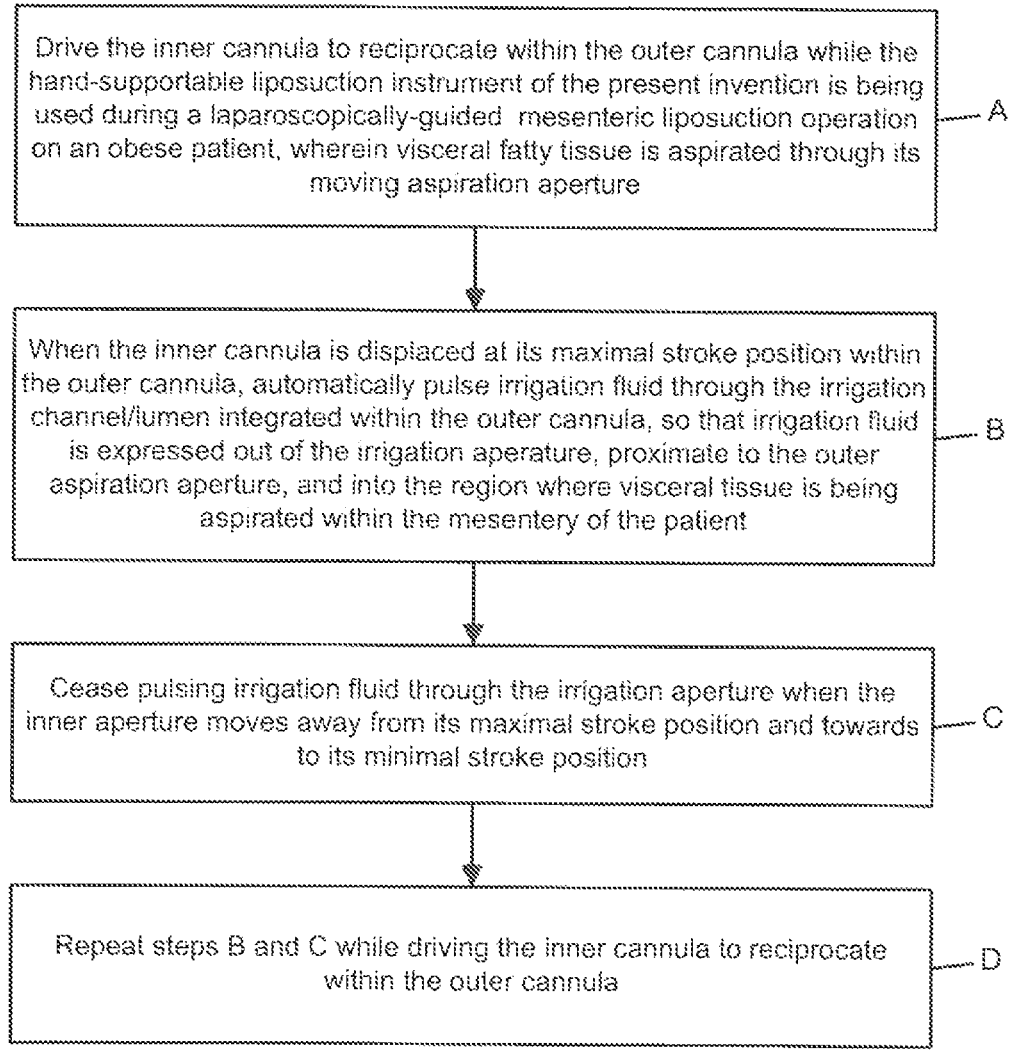
FIG. 2C is a flow chart describing the operation of the infusion pump of FIG. 1 in cooperation with irrigating electro-cauterizing visceral liposuction instrument illustrated in FIGS. 2A through 2B3.

FIG. 2C describes the primary control operations performed by system controller 4B during fluid irrigation delivery operations using the surgical system of FIG. 1. Specifically, as indicated at Step A in FIG. 2C, the inner cannula is driven to reciprocate within the outer cannula while the hand-supportable liposuction instrument is being used during a laparoscopically-guided mesenteric liposuction operation on an obese patient, wherein visceral fatty tissue is aspirated through its moving aspiration aperture. As indicated at Step B, when the inner cannula is displaced at its maximal stroke position within the outer cannula, irrigation fluid is automatically pulsed through the irrigation channel/lumen integrated within the outer cannula, so that irrigation fluid is expressed out of the irrigation aperture, proximate to the outer aspiration aperture, and into the region where visceral tissue is being aspirated within the mesentery of the patient. As indicated at Step C, the automatic pulsing of irrigation fluid through the irrigation aperture is ceased when the inner aperture moves away from its maximal stroke position and towards its minimal stroke position. As indicated at Step D, the operations of Steps B and C are repeated while driving the inner cannula to reciprocate within the outer cannula. The control routine of FIG. 2C will be realized using computer programming techniques well known in the art.

As shown in FIG. 2F, the laparoscopic instrumentation 2 will typically further include a laparoscope with a viewing portal and camera 2A, trochars for penetrating the abdomen, laparoscopic graspers, laparoscopic scissors, a laparoscopic bipolar cautery device, a CO2 infusion tube, as described in detail in U.S. Pat. No. 7,384,417 B2, incorporated herein by reference.

As shown in FIG. 2G, the infusion pump 4F will typically include a roller pump which compresses the tubing to create forward flow, as disclosed in U.S. Pat. No. 7,384,417 B2 incorporated herein by reference. More ideally the infusion pump 4F will be designed for a pulsatile flow of irrigation fluid through cannula 20 so that controlled amounts of fluid are delivered under short periods of time to facilitate synchronization with either the forward or return stroke of the inner cannula 5B.

Having described the preferred apparatus of the present invention, it is appropriate at this juncture to describe the preferred method of treating patients according to the present invention, with reference to the method flow chart set forth in FIG. 3.

Figure 3A:
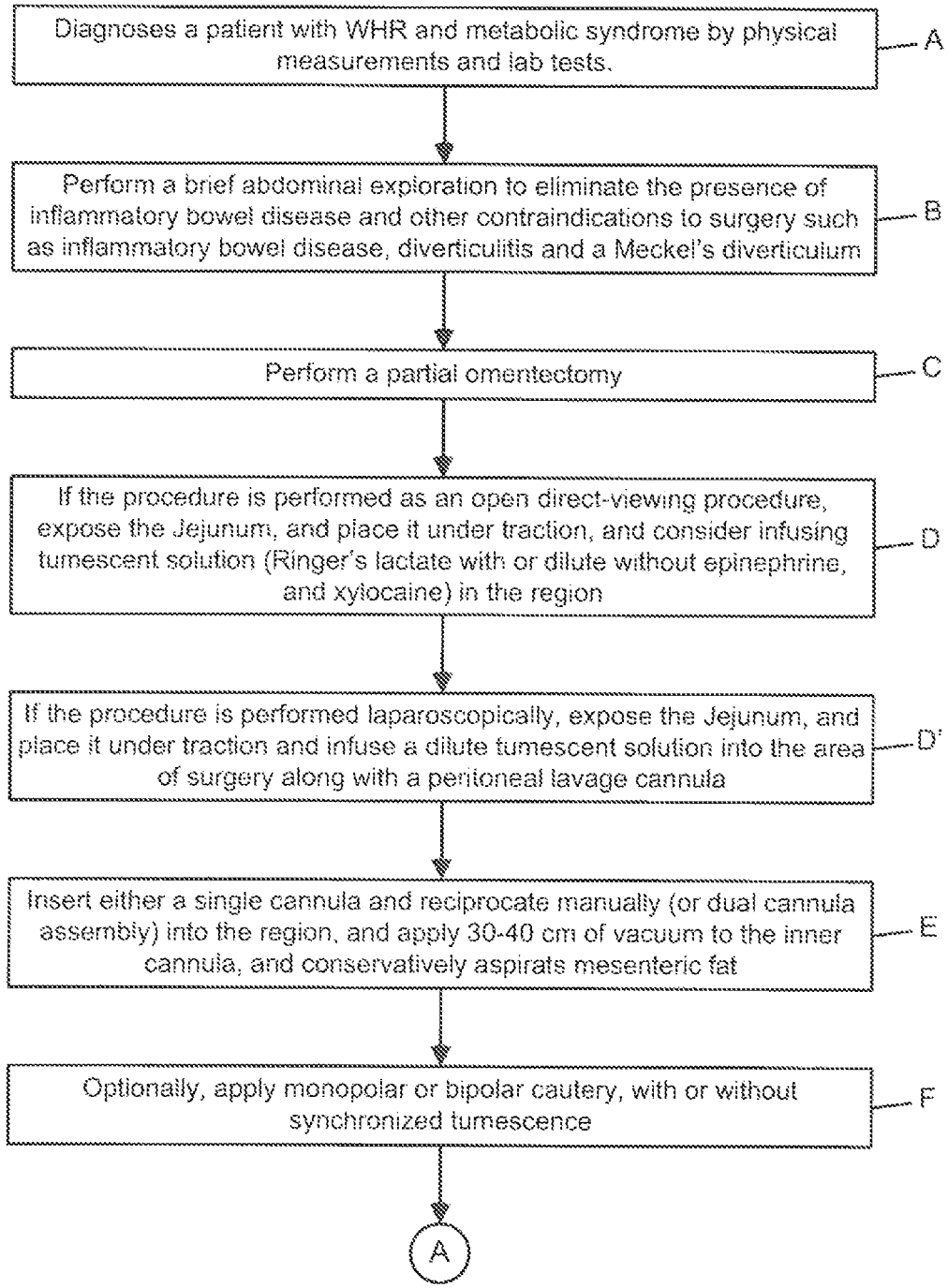
FIGS. 3A and 3B is a flow chart illustrating the primary steps carried out during the illustrative embodiment of the method of mesenteric liposuction according to the present invention, comprising diagnosis, exploration, partial omentectomy, small bowel mesenteric liposuction, large bowel mesenteric liposuction, followed by subcutaneous liposuction, abdominal and dermatolipectomies as indicated.

As indicated in Step A in FIG. 3A, the surgeon diagnoses a patient with metabolic syndrome and/or obesity, using the waist-to-hip ratio (WHR), by physical measurements and lab tests.

As indicated in Step B in FIG. 3A, the surgeon performs a brief abdominal exploration or inspection to eliminate the presence of inflammatory bowel disease and other contraindications to surgery, such as, diverticulitis and a Meckel's diverticulum, or any other pathology. At her option, the surgeon may infuse a tumescent solution (Ringer's lactate with or without dilute epinephrine, and with or without xylocaine) as described above to prepare the area for treatment.

As indicated in Step C in FIG. 3A, the surgeon performs a partial omentectomy by removing the redundant omental apron.

As indicated in Step D in FIG. 3A, when performed as an open direct-viewing procedure, the omentum is retracted and the jejunum is exposed. Either by the hands of an assistant in an open procedure or with aid of atraumatic laparoscopic graspers [Endo Babcock or Dolphin Nose Grasper], the proximal jejunum is isolated and placed under gentle tension. One atraumatic grasper is inserted in the right upper quadrant for retraction of the jejunum towards the liver, and a second atraumatic grasper is inserted in the left lower quadrant, placed on a section of jejunum approximately 6 to 8 inches distal to the previously placed grasper, and retracted caudally towards the left lower quadrant. The jejunum is placed under tension and the mesentery exposed and straightened.

As indicated at Step D in FIG. 3A, when performed as a laparoscopic procedure, a pneumoperitoneum is created in the usual fashion and the trochars are inserted so the procedure may be performed under laparoscopic guidance with multiple monitors. A partial omentectomy may be carried out by removing the caudal portions of the omentum. When performed laparoscopically, omentum is removed in strips to facilitate removal through laparoscopic portals. Care is taken to obtain strict hemostasis and to preserve an apron of protective omentum while it is substantially shortened and defatted.

FIG. 4 depicts the bowel grasped between two clamps to tent up the mesentery.

Figure 5:
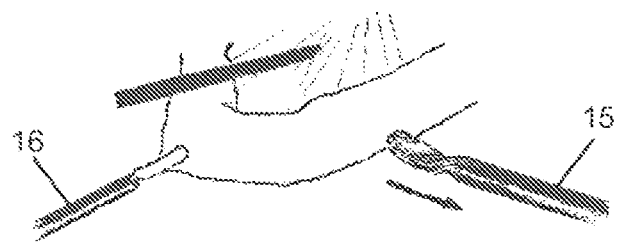
FIG. 5 is perspective view of the patient's abdominal region during a second phase of the mesenteric liposuction procedure of the present invention, showing the insertion of a cannula into the mesentery for infusion of tumescent solution.

FIG. 5 depicts a cannula inserted into the tented mesentery to infuse tumescent solution.

Figure 6:
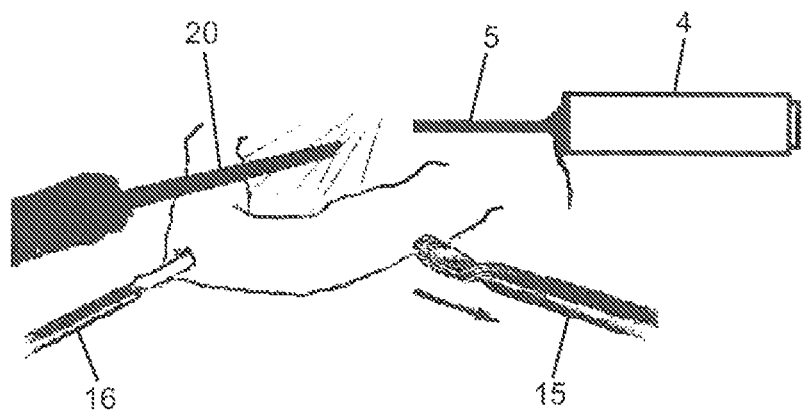
FIG. 6 is perspective view of the patient's abdominal region during a third phase of the mesenteric liposuction procedure of the present invention, showing the insertion of the bipolar electro-cauterizing twin-cannula liposuction instrument shown in FIG. 1, into the mesentery of the patient and fat removal by way of liposuction under laparoscopy guidance with the laparoscope shown.
Figure 7:
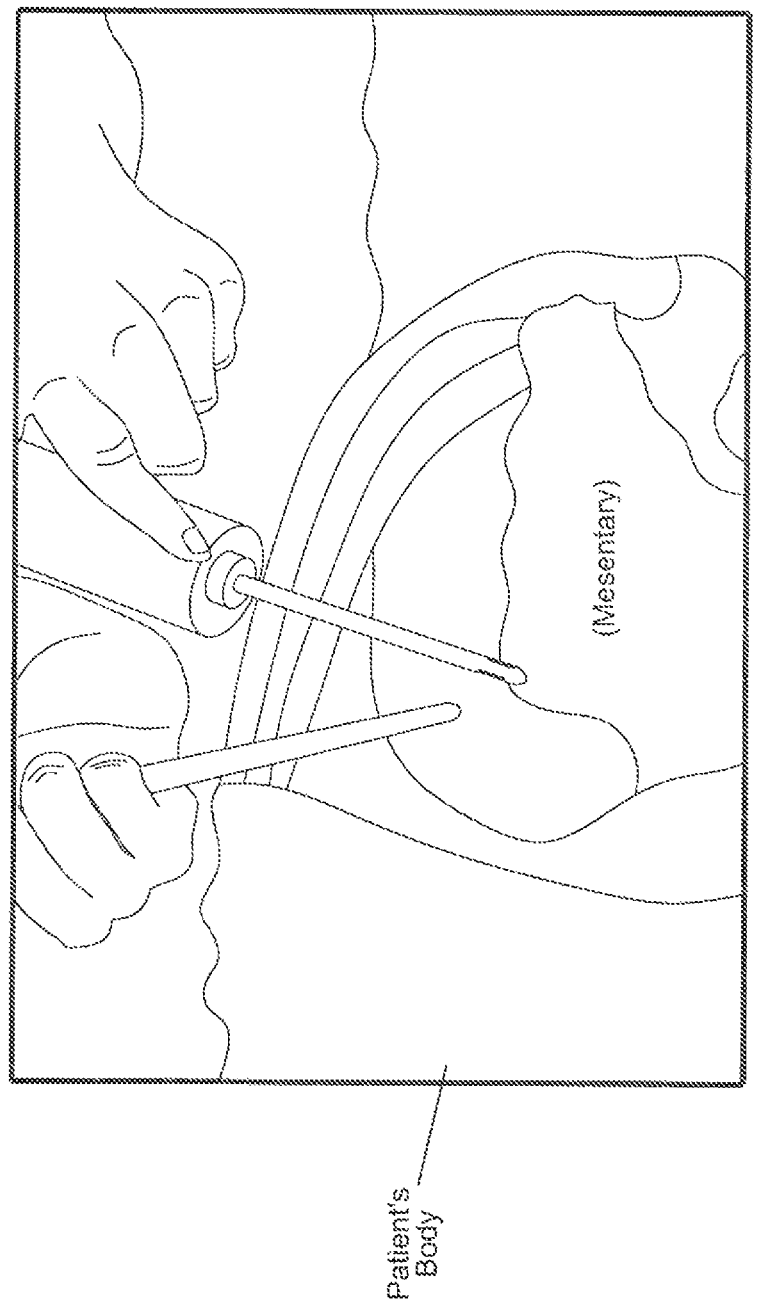
FIG. 7 is a cross-section partially cut away view of the patient's abdominal region during a later phase of the mesenteric liposuction procedure of the present invention, showing the aspiration and electro-cauterization of visceral fatty tissue in the mesentery, using the laparoscopically-guided irrigating bipolar electro-cauterizing twin-cannula liposuction instrumentation of the present invention.

As indicated in Step E in FIG. 3A, a retractor is inserted through the right lower quadrant and placed posteriorly beneath the tented mesentery. An incision is made anteriorly in the mesentery, approximately ⅔ of the distance between its base and the bowel. The surgeon then inserts either a single cannula through the right lower quadrant and into an anterior incision in the jejunal mesentery, and reciprocates it manually, or preferably inserts the power-assisted twin cannula assembly 5 into the region, and applies 30-40 cm Hg of vacuum to the inner cannula, and conservatively aspirates mesenteric fat. FIG. 6 depicts insertion of the twin cannula device 5 into the previously tumesced and tented mesentery.

When using a laparoscopically-guided electro-cauterizing twin-cannula liposuction instrument system shown in FIGS. 1 and 2, there is much less risk of vascular disruption or visceral injury than when using single cannula instrument, because the twin cannula instrument protects the adventitia of the arboreal blood vessels from injury, and allows treatment of larger areas more rapidly and effectively.

As indicated in Step F in FIG. 3A, the surgeon optionally, applies monopolar or bipolar cautery, with or without synchronized tumescence. By including a separate fluidic channel in the outer cannula, extending from its base to its tip, it is possible to synchronize a pulsed infusion of tumescent solutions or irrigation (e.g. lactated Ringer's solution with or without small amounts of epinephrine (e.g. 1:100,000-1:400,000) through this additional channel in the tip of the twin cannula assembly with the advancement of the inner cannula, to facilitate fat aspiration with a sump effect. Alternatively, a totally separate cannula may be placed with the mesentery and used for pulsatile or non-pulsatile, synchronized or unsynchronized infusion near the tip of the twin cannula assembly 5.

By eliminating the battering ram effect of a reciprocating cannula and the need for tumescent solution for hemostasis, twin cannula liposuction allows the minimally invasive removal of soft tissue in any location, including the intestinal mesentery by either open or laparoscopic approaches. Unlike single cannula liposuction cannulas, the tube-within-a-tube construction of the twin cannula assembly, taught in U.S. Pat. No. 7,384,417 B2 is particularly suited to a laparoscopic approach as all viscera are spared disruption from the moving member except the limited area of fat being aspirated in the mesentery adjacent to the outer cannula slot. The relatively stationary outer cannula reduces friction caused by the continually reciprocating inner cannula and the laparoscopy portal. Placement of the outer cannula 5A is positional, rather than actively reciprocating, to avulse particles of fat.

Twin cannula mesenteric liposuction (TCML) according to the principles of the present invention described above, thus allows direct correction of abdominal obesity, and in a less invasive and dramatically immediate fashion without the untoward nutritional consequences, hepatic, or renal complications of gastric bypass or banding procedures.

The use of twin cannula liposuction, with or without bipolar cautery hemostasis and with or without a synchronized pulsed infusion of tumescent or irrigation solution through the cannula, offers a controlled, rapid, and safer way of treating a length of intestine with much less risk of bleeding or vascular injury.

Although bipolar hemostasis obviates the need for tumescence with epinephrine containing solutions, small amounts of epinephrine could be added to small pulses of lactated Ringer's solution, with or without small quantities of local anaesthetic, which are synchronized with the advancement of the inner cannula within the outer cannula.

Since the irrigation solution is immediately aspirated through the aspiration aperture 55 of the twin (twin) cannula assembly 5 of FIG. 2A, the systemic effects of vasopressor and local anesthetics during twin cannula synchronized tumescence (TCST) would be more limited than an alternative means, such as infusion of a similarly dilute epinephrine and xylocaine in lactated Ringer's solution with a Tenckoff catheter via peritoneal lavage.

Epidural or general anaesthesia could replace or augment synchronized infusion or peritoneal lavage. Although TCST is the preferred embodiment of the described method, the present invention contemplates choosing modalities that are optimized for each individual patient's physiologic and cardiovascular status, and concentrations of xylocaine and epinephrine in the employed solutions from zero to therapeutic, as the situation dictates.

Figure 3B:
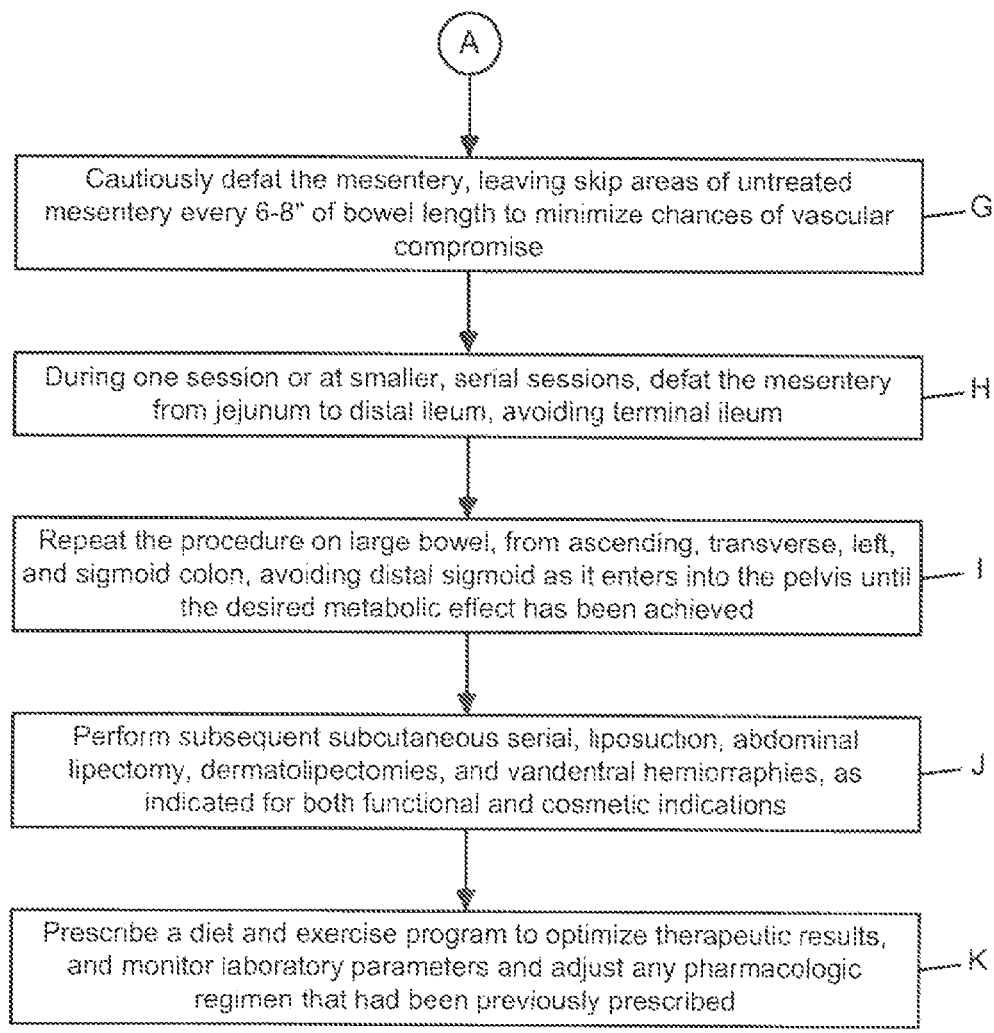

As indicated in Step G in FIG. 3B, the surgeon cautiously defats the mesentery, leaving skip areas of untreated mesentery every 6-8" of bowel length to minimize chances of vascular compromise. This step can be achieved by applying a vacuum of 30-40 cm Hg, and defatting the mesentery by reciprocating a single cannula manually, or in the preferred embodiment, initiating mechanical reciprocation of the inner cannula 5B within the outer cannula 5A of the transiently stationary twin cannula assembly 5. Care is taken to retain some fat and avoid creating defects that might allow intestine to herniate through, and any perforations in the mesentery are closed to eliminate this hazard. The area of treatment is inspected for hemostasis and any defects in the mesentery repaired. The jejunum between clamps is inspected for good vascular supply.

As indicated in Step H IN FIG. 3B, during a single session or during smaller, serial sessions, the surgeon defats the mesentery from jejunum to distal ileum, avoiding terminal ileum. Then, as with the open approach, a small area is skipped much like a radiating spokes on a wheel to assure continuity of blood supply, and the next 8" area of jejunum is tented and the procedure repeated until the terminal ileum is reached and left untreated. Any difficulties with hemostasis or questionable vascular viability of the bowel indicate the necessity of a resection and possible conversion to an open procedure.

As indicated in Step I in FIG. 3B, the surgeon repeats the procedure on the large bowel and/or the small bowel for greatest effect. The mesentery of the large bowel would be approached from the ascending colon to the sigmoid colon, avoiding the area surrounding the ileocecal valve, and the distal sigmoid colon as it descends into the pelvis, and the mesentery to any areas of large bowel which appear grossly involved with diverticulitis.

As indicated in Step J in FIG. 3B, the surgeon performs subsequent subcutaneous serial, liposuction, abdominal lipectomy, dermatolipectomies, and ventral herniorraphies, as indicated for both functional and cosmetic indications. Large volume subcutaneous liposuction, panniculectomy, abdominoplasty, repair of any ventral hernias or diastasis recti could be carried out in serial sessions to obtain a much tightened abdominal corset for both functional and cosmetic improvement. The majority of these procedures can be performed under conscious sedation and on an ambulatory basis on these patients with minimal complications because of their improved metabolic profiles.

As indicated in Step K in FIG. 3B, the surgeon prescribes a diet and exercise program to optimize therapeutic results, and monitors laboratory parameters and adjust any pharmacologic regimen that had been previously prescribed.

Several modifications to the illustrative embodiments have been described above. It is understood, however, that various other modifications to the illustrative embodiment of the present invention will readily occur to persons with ordinary skill in the art. All such modifications and variations are deemed to be within the scope and spirit of the present invention as defined by the accompanying Claims to Invention.

What is claimed is:
1. A method of ameliorating metabolic syndrome and/or abdominal obesity in a patient by performing intra-abdominal visceral fat tissue aspiration, wherein the patient has an abdominal region and a mesenteric region, said method comprising the steps of:
(a) creating laparoscopy portals in a patient, and infusing an inert gas into the abdominal region of the patient to cause abdominal distension;
(b) inserting a laparoscope into the abdominal region of the patient so that a surgeon can capture video images of the abdominal region of the patient, and display the captured video images within the view of the surgeon;

(c) inserting a bipolar electro-cauterizing twin-cannula tissue aspiration instrument, into the mesenteric region of the patient, wherein said bipolar electro-cauterizing twin-cannula tissue aspiration instrument has an instrument housing and a twin cannula assembly including an inner cannula reciprocating within an outer cannula mounted stationary with respect to said instrument housing; and (d) using laparoscopic guidance obtained from the video images of the mesenteric region of the patient, captured by said laparoscope, (i) aspirating visceral fat tissue from the mesenteric region of the patient, using said bipolar electro-cauterizing twin-cannula tissue aspiration instrument, while (ii) simultaneously infusing a tumescent solution into the mesenteric region of said patient, through said twin cannula assembly, while synchronizing said infusion of tumescent solution with the forward or return stroke of the inner cannula within said outer cannula, during operation of bipolar electro-cauterizing twin-cannula aspiration instrument.

2. The method of claim 1, wherein said step (b) further comprises displaying said video images of the abdominal region of the patient on a display screen within the view of the surgeon.

3. The method of claim 1, wherein during step (d), said instrument housing comprises a hand-held housing adapted to fit within a hand of said surgeon.

4. The method of claim 1, wherein during step (a), said inert gas is $CO_2$ gas.

* * * * *